United States Patent [19]

Strong et al.

[11] 4,174,959

[45] Nov. 20, 1979

[54] BENZIMIDAZOLE COMPOUNDS

[75] Inventors: Philip L. Strong, Anaheim, Calif.; Wayne S. Belles, Moscow, Id.

[73] Assignee: United States Borax & Chemical Corporation, Los Angeles, Calif.

[21] Appl. No.: 899,129

[22] Filed: Apr. 24, 1978

[51] Int. Cl.$^2$ ...................... A01N 9/22; C07D 235/14
[52] U.S. Cl. ........................................ 71/92; 548/325; 548/330; 548/332; 548/333; 548/334; 542/422
[58] Field of Search ............... 548/325, 330, 332, 333, 548/334; 542/422; 71/92

[56] References Cited

U.S. PATENT DOCUMENTS

| | | | |
|---|---|---|---|
| 3,531,495 | 9/1970 | Burton et al. | 548/332 |
| 3,901,910 | 8/1975 | Hunter et al. | 548/305 |
| 3,954,438 | 5/1976 | Hunter et al. | 71/92 |

*Primary Examiner*—John M. Ford
*Assistant Examiner*—Robert C. Whittenbaugh
*Attorney, Agent, or Firm*—James R. Thornton

[57] ABSTRACT

Aldimine and ketimine derivatives of 7-aminobenzimidazoles are provided. The compounds are useful as herbicides and can be applied pre-emergent or post-emergent to weeds.

18 Claims, No Drawings

BENZIMIDAZOLE COMPOUNDS

This invention relates to a novel class of benzimidazole derivatives which are useful as herbicides, such as for controlling weeds in crops.

BACKGROUND OF THE INVENTION

Various substituted benzimidazoles are known to be useful as herbicides. U.S. Pat. No. 3,325,271 describes the use as herbicides of a broad class of substituted benzimidazoles in which there is at least one substituent on the aromatic ring or at the 1- or 2-position of the molecule. The aromatic substituents may be selected from nitro, halo, lower alkyl, lower alkoxy and halo-lower alkyl. U.S. Pat. Nos. 3,901,910 and 3,954,438 describe a specific group of 5-trifluoromethyl-7-aminobenzimidazoles which have herbicidal activity.

SUMMARY OF THE INVENTION

The present invention provides a novel class of aldimine and ketimine derivatives of 7-aminobenzimidazoles corresponding to the following formula:

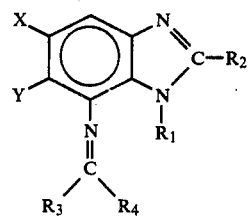

in which $R_1$ and $R_2$ are each selected from hydrogen, lower alkyl, halo-lower alkyl, lower cycloalkyl, lower alkoxy-lower alkyl, hydroxy-lower alkyl and dilower alkylamino, $R_3$ represents hydrogen, lower alkyl, or monocyclic aryl, $R_4$ represents lower alkyl, lower alkenyl or monocyclic aryl, X represents halo, lower alkyl, halo-lower alkyl, lower alkylsulfonyl or halo-lower alkylsulfonyl, and Y represents hydrogen, halo or lower alkoxy. $R_3$ and $R_4$ combined may also represent an alkylene group having from 3 to about 7 carbon atoms in the chain. Further, $R_1$ and $R_2$ may not both be hydrogen. The compounds of this invention possess excellent herbicidal activity, both pre-emergent and post-emergent. Many of the compounds possess substantial solubility in organic solvents so that they may be formulated readily as emulsifiable concentrates.

The lower alkyl, lower alkoxy, lower cyloalkyl, lower alkylsulfonyl, and lower alkenyl groups which may be represented by $R_1$, $R_2$, $R_3$, $R_4$, X and/or Y in the above formula contain up to about eight carbon atoms and, preferably, in the case of $R_1$, $R_2$, X and Y, up to about four carbon atoms. Examples of such groups include methyl, ethyl, n-propyl, isopropyl, n-butyl, tert.-butyl, sec.-butyl, sec.-pentyl, n-hexyl, cyclohexyl, cyclopropyl, 2-butenyl, 2-ethylhexyl, 1-methyl-butenyl-2, 2-pentenyl, methoxy, methylsulfonyl, ethylsulfonyl, ethoxy, and the like. It is preferred that the lower alkyl groups which may be represented by X are branched-chain alkyls such as isopropyl, tert.-butyl, sec.-butyl, and the like. Halo groups which may be represented by X or Y include chloro, bromo, fluoro, etc. and such halo groups also may be substituents on the lower alkyl and alkylsulfonyl groups represented by X. Examples of such halogenated groups include trifluoromethyl, perfluoroethyl, difluoromethylsulfonyl, trifluoromethyl-sulfonyl, dichloromethyl, bromoethyl, perfluoroethylsulfonyl, and the like. Examples of alkylene groups which may be represented by $R_3$–$R_4$ combined include trimethylene, tetramethylene, pentamethylene, hexamethylene and 3-methylpentamethylene.

$R_3$ and $R_4$ may also represent a monocyclic aryl group which may optionally contain one or more nitro, halo, lower alkyl or lower alkoxy substituents. Examples of such groups include phenyl, 4-chlorophenyl, 4-nitrophenyl, 4-methoxyphenyl, 2,5-dimethoxyphenyl, 2,4-dichlorophenyl, 4-ethoxyphenyl, 3,4-dichlorophenyl, 3-bromophenyl, 2-chloro-5-nitrophenyl, 5-bromo-2-methoxyphenyl, 4-fluorophenyl, pentafluorophenyl, 3-methylphenyl, 4-ethylphenyl, 2,4-dimethylphenyl, 2-chloro-4-methylphenyl, and the like.

Preferably, $R_1$ and $R_2$ represent lower alkyl or halo-lower alkyl, X represents trifluoromethyl, methylsulfonyl or fluorinated methylsulfonyl, and Y represents chloro or hydrogen.

The compounds of this invention are readily prepared by reaction of the corresponding 7-aminobenzimidazole compound with an aldehyde or ketone according to the following equation:

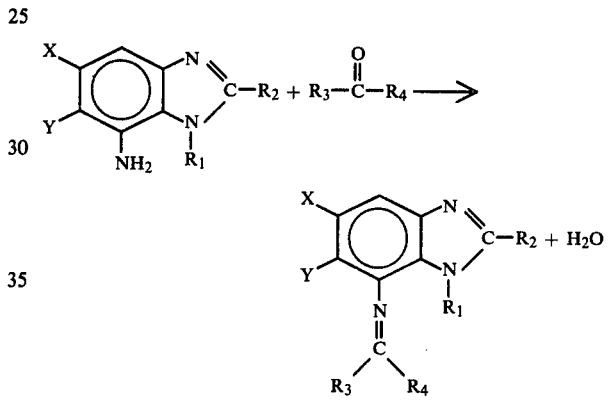

in which $R_1$, $R_2$, $R_3$, $R_4$, X and Y have the significance previously assigned. The reaction takes place at elevated temperatures, preferably in the presence of a solvent with which the by-product, water, will form an azeotrope. Preferably, a small amount of acid, such as sulfuric acid or benzenesulfonic acid, is present as a catalyst. The progress of the reaction can be followed by measuring the amount of the by-product, water, which is removed from the reaction vessel by means of an apparatus such as a Dean-Stark trap.

Suitable solvents include toluene, xylene, and benzene. The reaction is preferably run at reflux temperatures. The products are readily separated from the reaction mixture by removing the solvent and may be formulated as such or, if desired, may be purified by known procedures such as distillation under reduced pressure or recrystallization.

The following examples illustrate preparation of representative compounds of this invention.

EXAMPLE 1

7-(pentylidene-3-amino)-1-isopropyl-2-methyl-5-trifluoromethyl-benzimidazole

A round-bottom reaction flask equipped with a Dean-Stark trap and condenser was charged with 4.0 grams (0.015 mole) of 1-isopropyl-2-methyl-5-trifluoromethyl-7-aminobenzimidazole, 50 ml. of toluene and 2 drops of concentrated sulfuric acid. To this stirred mixture was added 6.03 grams (0.07 mole) of 3-pentanone. The stirred solution was heated at reflux temperature for 81 hours, removing by-product water in the trap. The cooled solution was then dried over anhydrous sodium sulfate. The sodium sulfate was removed by filtration and the solvent then removed from the filtrate by distillation under reduced pressure. The residue was distilled under reduced pressure and the product collected at 149°–155° C./0.18 mm. The yield was 2.6 g. (52%).

EXAMPLE 2

7-(alpha-methylbenzylidenamino)-1-isopropyl-2-methyl-5-trifluoromethylbenzimidazole Acetophenone (2.8 g.) was reacted with 1-isopropyl-2-methyl-5-trifluoromethyl-7-aminobenzimidazole (4.0 g.) in 50 ml. of xylene for 21 hours according to the procedure of Example 1. After drying over sodium sulfate, the solvent was removed and the crude residue was recrystallized from benzene-cyclohexane (1:1) to give 3.38 g. of the desired product, m.p. 164°–166° C.

EXAMPLE 3

7-benzylidenamino-1-ethyl-2-methyl-5-trifluoromethyl-6-chlorobenzimidazole

Benzaldehyde (0.78 g.; 7.35 mmole) was reacted with 1-ethyl-2-methyl-5-trifluoromethyl-6-chloro-7-aminobenzimidazole (1.0 g.; 3.66 mmole) in the presence of 7 ml. of xylene and a few crystals of benzenesulfonic acid. The mixture was refluxed for 1 hour, removing water from the reaction mixture. Upon cooling to room temperature, the product crystallized out of solution to give 1.24 g. (94% yield). After recrystallization from benzene, the product melts at 183°–185.5° C.

EXAMPLE 4

7-(5-methylhexylidene-2-amino)-6-chloro-1-ethyl-2-methyl-5-trifluoromethylbenzimidazole A solution of 5.0 g. (0.015 mole) of 1-ethyl-2-methyl-5-trifluoromethyl-6-chloro-7-aminobenzimidazole, 10 g. (0.09 mole) of methylisoamylketone and 3 drops of concentrated sulfuric acid in 15 grams of xylene was heated at reflux temperature using a Dean-Stark trap for 20 hours. A total of 0.5 ml. of by-product water was collected. The reaction mixture was then evaporated to dryness under reduced pressure. The residue (6.68 g.) was distilled under reduced pressure. After a forecut, the desired product was collected at 181°–184° C./0.7 mm. (1.36 g.).

The intermediate 7-aminobenzimidazoles can be prepared by general synthetic procedures well-known to the art. See also U.S. Pat. Nos. 3,325,271, 3,412,101, 3,901,910 and 3,954,438 and Chem. Abstracts 72, 31366 for detailed examples of preparation. Co-pending application Ser. No. 844,777 filed Oct. 25, 1977 by Hunter et al. describes preparation of 5-alkylsulfonyl and fluoroalkylsulfonyl benzimidazoles.

EXAMPLES 5–33

The following are representative examples of other compounds embraced by the present invention which may be prepared by the procedures described above.

5. 7-(2-ethylbutylidene-1-amino)-1-isopropyl-2-methyl-5-trifluoromethylbenzimidazole, b. p. 156°–159° C./0.18 mm.

6. 7-(2-ethylhexanylidene-1-amino)-1-ethyl-2-methyl-5-trifluoromethyl-6-chlorobenzimidazole, m. p. 73.5°–75.5° C.

7. 7-(2-methyl-2-pentenylidene-1-amino)-1-ethyl-2-methyl-5-trifluoromethyl-6-chlorobenzimidazole, m. p. 105° C.

8. 7-(heptylidene-1-amino)-1-ethyl-2-methyl-5-trifluoromethyl-6-chlorobenzimidazole, m. p. 165°–173° C. (softens 155° C.)

9. 7-(propylidene-2-amino)-1-ethyl-2-methyl-5-trifluoromethyl-6-chlorobenzimidazole, b. p. 166°–168° C./0.5 mm.

10. 7-cyclohexylidenamino-1-ethyl-2-methyl-5-trifluoromethyl-6-chlorobenzimidazole, b. p. 210° C./0.8 mm.

11. 7-(pentylidene-3-amino)-1-ethyl-2-methyl-5-trifluoromethyl-6-chlorobenzimidazole, amber glass 12. 7-(5-methylhexylidene-2-amino)-1-isopropyl-2-methyl-5-trifluoromethylbenzimidazole, b. p. 159°–161° C./0.4 mm.

13. 7-(5-methylhexylidene-2-amino)-1-isopropyl-2-methyl-5-trifluoromethyl-6-chlorobenzimidazole, b. p. 180°–185° C./0.5 mm.

14. 7-(para-methoxybenzylidenamino)-1-isopropyl-2-methyl-5-trifluoromethylbenzimidazole, m. p. 144°–146° C.

15. 7-(para-nitrobenzylidenamino)-1-isopropyl-2-methyl-5-trifluoromethylbenzimidazole, m. p. 204°–206° C.

16. 7-benzylidenamino-1-isopropyl-2-methyl-5-difluoromethylsulfonylbenzimidazole, m. p. 186.5°–187.5° C.

17. 7-(3,4-dichlorobenzylidenamino)-1,2-dimethyl-5-trifluoromethylsulfonylbenzimidazole 18. 7-(pentylidene-3-amino)-1-methyl-2-trifluoromethyl-5-isopropylbenzimidazole 19. 7-(alpha-methyl-2,4-dichlorobenzylidenamino)-1-cyclohexyl-5-trifluoromethylbenzimidazole 20. 7-isobutylidenamino-1-methyl-2-isopropyl-5-tert.-butyl-6-chlorobenzimidazole 21. 7-(beta-methyl-2-pentenylidene-1-amino)-2,5-bis-trifluoromethylbenzimidazole 22. 7-benzylidenamino-1-methyl-2-ethyl-5-trifluoromethyl-6-methoxybenzimidazole 23. 7-cyclohexylidenamino-1-methyl-2-isopropyl-5-ethylsulfonylbenzimidazole 24. 7-(para-methylbenzylidenamino)-1,2,5-trimethyl-6-bromobenzimidazole 25. 7-(6-methyl-5-heptenylidene-1-amino)-1-ethyl-2-methyl-5-difluoromethylsulfonylbenzimidazole 26. 7-(butenylidene-2-amino)-1-ethyl-2-hydroxymethyl-5-trifluoromethyl-6-chlorobenzimidazole 27. 7-(3-methylcyclohexylidenamino)-1-isopropyl-2-dimethylamino-5-trifluoromethyl-6-chlorobenzimidazole 28. 7-(3-methyl-4-methoxybenzylidenamino)-1-(2-bromoethyl)-2-methyl-5-trifluoromethyl-6-chlorobenzimidazole 29. 7-(alpha-phenyl-4-nitrobenzylidenamino)-1-ethyl-2-methyl-5-chlorobenzimidazole 30. 7-(alpha-methyl-2,4-dimethoxybenzylidenamino)-1-methyl-2-ethyl-5-methylsulfonyl-6-chlorobenzimidazole 31. 7-(3-butenylidene-2-amino)-1-(2-methoxy-1-methylethyl)-2-methyl-5-trifluoromethylbenzimidazole 32. 7-(2,4-dichlorobenzylidenamino)-2-trifluoromethyl-5-ethyl-6-bromobenzimidazole 33. 7-isobutylidenamino-1-cyclopropyl-2-methyl-5-trifluoromethyl-6-chlorobenzimidazole The benzimidazole derivatives of this invention are relatively resistant to hydrolysis. For example, no significant hydrolysis was found when they were stirred in 95% ethanol at room temperature. However, they do hydrolyze slowly at reflux temperature in 95% ethanol and rapidly in the presence of mineral acid.

The compounds of this invention are excellent herbicides and can be applied as either a pre-emergent or post-emergent treatment; that is, they can be applied to soil in which the weeds will grow to kill or suppress the emergence of seedlings of undesirable plants or they can be applied to the foliage of the growing plants after emergence from the soil. Thus, the compounds can be used to control the growth of weeds by applying a phytotoxic amount of one or more of the active compounds of this invention to the locus to be protected; that is, soil in which the weeds are growing or will grow or the foliage of the growing plants. When used as a pre-emergence treatment, the compounds can be incorporated, if desired, such as by mixing into the top 1 to 3 inches (2.5 to 7.6 cm.) of the soil, prior to planting the crop. When used as a post-emergence treatment, it is preferred that a directed spray be employed, thereby directing the application of the herbicide onto the foliage of the weeds and away from the foliage of the crop plants. Weeds, as used herein, is meant to include any plant growth which is undesirable.

The compounds are especially useful as post-emergence herbicides for selectively controlling weeds in the presence of desirable crops such as peanuts, corn and rice. The weeds controlled include many of the broadleaf and grassy weeds such as jimsonweed, lambsquarter, mustard, pigweed, sesbania, prickly sida, velvetleaf, morningglory, cocklebur, foxtail, etc.

Generally, an application rate of from about 0.2 to about 10 pounds (about 0.1 to 5 kg.) of one or more of the active compounds per acre is effective in controlling weed growth. Preferably, an application rate in the range of about 0.5 to 4 pounds (about 0.2 to 2 kg.) per acre is used as a post-emergence treatment.

The following examples illustrate the herbicidal activity of representative compounds of this invention.

EXAMPLE 34

The compounds to be tested were evaluated as both a pre-emergent and post-emergent treatment. Greenhouse pots were planted to soybeans (SO), velvetleaf (VL), oats (O) and millet (M). The pots were sprayed on the same day as planting with an ethanol-dioxane solution of the compound to be tested at a rate of 5 pounds per acre. Another set of pots with the same plants was treated after the plants had emerged and were about one inch in height. These pots were also sprayed with the solution of the compound to be tested at a rate of 5 pounds per acre. The pots were kept in the greenhouse and watered when needed. Twenty-one days after treatment, the pots were examined and the plants rated for herbicidal activity on a 0–9 scale in which 0 = no effect 1 = <10% injury 2 = 10–40% injury 3 = 40–70% injury 4 = >70% injury 5 = <25% kill 6 = 25–50% kill 7 = 50–75% kill 8 = 75–99% kill 9 = 100% kill The results are shown in Table I.

TABLE I

| | Herbicidal Activity | | | | | | | |
|---|---|---|---|---|---|---|---|---|
| | Pre | | | | Post | | | |
| Compound | SO | VL | O | M | SO | VL | O | M |
| Example 1 | 8 | 9 | 9 | 9 | 9 | 9 | 9 | 9 |
| Example 2 | 0 | 0 | 0 | 0 | 0 | 9 | 0 | 9 |
| Example 3 | 0 | 0 | 0 | 0 | 3 | 9 | 2 | 5 |
| Example 4 | 0 | 0 | 0 | 5 | 9 | 9 | 9 | 9 |
| Example 5 | 6 | 9 | 9 | 9 | 8 | 9 | 9 | 9 |
| Example 6 | 1 | 0 | 0 | 0 | 8 | 9 | 5 | 9 |
| Example 7 | 2 | 0 | 0 | 0 | 6 | 9 | 6 | 9 |
| Example 8 | 3 | 0 | 0 | 0 | 2 | 9 | 2 | 0 |
| Example 9 | 3 | 9 | 6 | 9 | 9 | 9 | 9 | 9 |
| Example 10 | 1 | 6 | 0 | 6 | 9 | 8 | 9 | 9 |
| Example 11 | 1 | 6 | 0 | 5 | 9 | 8 | 9 | 9 |
| Example 12 | 1 | 5 | 3 | 6 | 0 | 9 | 9 | 9 |
| Example 13 | 0 | 0 | 0 | 0 | 6 | 9 | 9 | 9 |
| Example 14 | 0 | 9 | 0 | 1 | 2 | 9 | 9 | 9 |
| Example 15 | 0 | 0 | 0 | 0 | 2 | 9 | 1 | 5 |

EXAMPLE 35

Several compounds were evaluated as post-emergence herbicides in greenhouse tests with a broad group of crops and weeds. Greenhouse pots containing the plants were sprayed with an ethanol-dioxane solution of the compounds at a rate of 1 pound per acre when the plants were about one inch in height. Twenty-one days after treatment, the plants were rated on a 0 to 9 scale as described in Example 34. Where two numbers are used, i.e. 8/4, the first number represents the percent kill and the second number is the injury to the remaining plants. The results are given in Table II and are an average of two replicates.

TABLE II

| | Activity - Post | | | | |
|---|---|---|---|---|---|
| Plant Species | Cmpd. 2 | Cmpd. 5 | Cmpd. 12 | Cmpd. 13 | Cmpd. 14 |
| alfalfa | 8 | 9 | 9 | 9 | 5/1 |
| corn | 0/1 | 0 | 0 | 0 | 0 |
| cotton | 9 | 8 | 9 | 9 | 9 |
| dry beans | 0/1 | 8/4 | 8/4 | 9 | 5/1 |
| peanuts | 0/1 | 0/1 | 0/1 | 0/1 | 0/1 |
| rice | 0 | 0 | 0/1 | 5/1 | 0 |
| soybeans | 0/1 | 0/1 | 0/3 | 8/4 | 0/2 |
| wheat | 0 | 0 | 5/1 | 6/2 | 0 |
| cocklebur | 8/2 | 9 | 9 | 9 | 5/0 |
| jimsonweed | 6/0 | 8/1 | 6/2 | 6/1 | 0 |
| lambsquarters | 8/1 | 9 | 9 | 9 | 5/1 |
| morningglory | 9 | 9 | 9 | 9 | 0/2 |
| mustard | 8/3 | 8/4 | 8/4 | 8/4 | 8/1 |
| prickly sida | 0/1 | 8/2 | 9 | 8/4 | 7/0 |
| pigweed | 8/2 | 8/3 | 9 | 9 | 6/2 |
| sesbania | 0 | 8 | 9 | 8/4 | 0 |
| velvetleaf | 6/0 | 9 | 8/2 | 9 | 0/1 |
| barnyardgrass | 0 | 0 | 5/1 | 9 | 0 |
| foxtail | 0 | 0 | 8/4 | 9 | 0 |
| Johnsongrass | 0/2 | 5/2 | 5/1 | 6/1 | 0 |
| wild oats | 0 | 0 | 6/1 | 6/1 | 0 |

TABLE II-continued

| Plant Species | Activity - Post | | | | |
|---|---|---|---|---|---|
| | Cmpd. 2 | Cmpd. 5 | Cmpd. 12 | Cmpd. 13 | Cmpd. 14 |
| ragweed | — | — | 9 | 8/4 | — |

Since a relatively small amount of one or more of the active compounds should be uniformly distributed over the area to be treated, the compounds preferably are formulated with conventional herbicide carriers, either liquid or solid. Thus, the compounds can be impregnated on or admixed with a pulverulent solid carrier such as lime, talc, clay, Bentonite, calcium chloride, vermiculite, and the like. Alternatively, the compounds can be dissolved or suspended in a liquid carrier such as water, kerosene, alcohols, diesel oil, mineral oil, xylene, benzene, glycols, ketones and the like.

A surfactant is preferably included to aid in dispersion, emulsification and coverage. The surfactant can be ionic or non-ionic and may be liquid or a solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of naphthalenesulfonic acid, alkylaryl polyether alcohols, long chain quaternary ammonium compounds, sodium salts of petroleum-derived alkylsulfonic acids, organophosphates, polyoxyethylene-sorbitan monolaurate, and the like. These dispersing and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 95 percent by weight of one or more of the active compounds with a carrier or diluent, which may be a liquid or a solid. Liquid carriers in which the active agent is soluble or other liquids in which the compound may be suspended or dispersed, can be used. A surfactant is also generally included to facilitate such dilution or dispersion in water. However, the surfactant itself may comprise the carrier in such concentrates.

The herbicidal compositions can include other beneficial adjuvants, such as humectants, oils and contact agents. Further, other herbicides such as the chlorophenoxyacetic acids, substituted uracils and ureas, dinitroanilines, phenylenediamines, thiocarbamates, carbamates, anilides, amides, and haloalkanoic acids, can be included in the formulation, if desired.

Various changes and modifications of the invention can be made, and, to the extent that such variations incorporate the spirit of this invention, they are intended to be included within the scope of the appended claims.

What is claimed is:

1. A compound of the formula

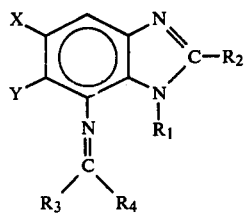

wherein $R_1$ and $R_2$ are each selected from the group consisting of hydrogen, lower alkyl, halo-lower alkyl, lower cycloalkyl, lower alkoxy-lower alkyl, hydroxy-lower alkyl and dilower alkylamino, $R_3$ is selected from hydrogen, lower alkyl and monocyclic aryl, $R_4$ is selected from lower alkyl, lower alkenyl and monocyclic aryl, or $R_3$–$R_4$ taken together represent alkylene of about 3 to 7 carbon atoms, X is selected from halo, lower alkyl, halo-lower alkyl, lower alkylsulfonyl, and halo-lower alkylsulfonyl, and Y is hydrogen, halo or lower alkoxy, in which not more than one of said $R_1$ and $R_2$ represents hydrogen and wherein said monocyclic aryl is selected from phenyl, nitrophenyl, halophenyl, lower alkylphenyl and lower alkoxyphenyl groups.

2. A compound according to claim 1 in which $R_1$ and $R_2$ are lower alkyl of up to about 4 carbon atoms.

3. A compound according to claim 1 in which X is trifluoromethyl, methylsulfonyl or fluorinated-methylsulfonyl.

4. A compound according to claim 1 in which said Y is hydrogen or chloro.

5. The compound according to claim 1, 7-(5-methylhexylidene-2-amino)-1-isopropyl-2-methyl-5-trifluoromethylbenzimidazole.

6. The compound according to claim 1, 7-(5-methylhexylidene-2-amino)-1-isopropyl-2-methyl-5-trifluoromethyl-6-chlorobenzimidazole.

7. A compound according to claim 1 in which said $R_3$ and $R_4$ are lower alkyl.

8. An herbicidal composition comprising an herbicidally effective amount of a compound according to claim 1, a surfactant, and an inert carrier therefor.

9. The method for controlling weed growth which comprises applying to the locus of said weeds a phytotoxic amount of a compound of the formula of claim 1.

10. The method according to claim 9 in which said compound is applied as a post-emergence treatment at a rate of about 0.5 to 4 pounds per acre.

11. The method according to claim 9 in which said $R_3$ and $R_4$ are lower alkyl.

12. The method according to claim 9 in which said $R_1$ and $R_2$ are lower alkyl of up to 4 carbon atoms, said X is selected from trifluoromethyl, methylsulfonyl and fluorinated methylsulfonyl, and said Y is hydrogen or chloro.

13. The method according to claim 9 in which said compound is 7-(5-methylhexylidene-2-amino)-1-isopropyl-2-methyl-5-trifluoromethylbenzimidazole.

14. The method according to claim 9 in which said compound is 7-(5-methylhexylidene-2-amino)-1-isopropyl-2-methyl-5-trifluoromethyl-6-chlorobenzimidazole.

15. The compound according to claim 1, 7-(pentylidene-3-amino)-1-isopropyl-2-methyl-5-trifluoromethylbenzimidazole.

16. The compound according to claim 1, 7-(propylidene-2-amino)-1-ethyl-2-methyl-5-trifluoromethyl-6-chlorobenzimidazole.

17. The compound according to claim 1, 7-cyclohexylidenamino-1-ethyl-2-methyl-5-trifluoromethyl-6-chlorobenzimidazole.

18. The compound according to claim 1, 7-benzylidenamino-1-isopropyl-2-methyl-5-difluoromethylsulfonylbenzimidazole.

* * * * *